United States Patent
Presedo

[11] Patent Number: 6,075,174
[45] Date of Patent: Jun. 13, 2000

[54] BF₃ REMOVAL FROM BF₃ CATALYZED OLEFIN OLIGOMER

[75] Inventor: Hector Presedo, Baton Rouge, La.

[73] Assignee: BP Amoco Corporation, Chicago, Ill.

[21] Appl. No.: 08/436,696

[22] Filed: May 8, 1995

[51] Int. Cl.⁷ .................................. C07C 2/02
[52] U.S. Cl. ..................... 585/525; 585/504; 502/31; 502/56
[58] Field of Search ............... 502/31, 56; 585/504, 585/525

[56] References Cited

U.S. PATENT DOCUMENTS

| | | | |
|---|---|---|---|
| 2,148,115 | 2/1939 | Gerhart et al. | 196/10 |
| 2,148,116 | 2/1939 | Gerhart et al. | 196/10 |
| 2,412,595 | 12/1946 | Axe | 260/671 |
| 2,425,745 | 8/1947 | Leonard et al. | 260/683.4 |
| 2,528,876 | 11/1950 | Evering et al. | 260/683.15 |
| 2,644,017 | 6/1953 | McCaulay et al. | 260/671 |
| 2,927,129 | 3/1960 | Hennig et al. | 260/501 |
| 2,971,992 | 2/1961 | Bloch | 260/671 |
| 3,000,964 | 9/1961 | Milligan | 260/624 |
| 3,113,167 | 12/1963 | Sauer | 260/683.15 |
| 3,149,178 | 9/1964 | Hamilton et al. | 260/683.9 |
| 3,330,883 | 7/1967 | Giannetti et al. | 260/683.15 |
| 3,363,986 | 1/1968 | Guarnaccio | 23/205 |
| 3,382,291 | 5/1968 | Brennan | 260/683.15 |
| 3,929,749 | 12/1975 | Cooper et al. | 260/86.7 |
| 4,017,548 | 4/1977 | Petrille | 260/606.5 B |
| 4,020,121 | 4/1977 | Kister et al. | 260/683.15 D |
| 4,213,001 | 7/1980 | Madgavkar et al. | 585/510 |
| 4,238,417 | 12/1980 | Austin et al. | 568/385 |
| 4,239,930 | 12/1980 | Allphin et al. | 585/517 |
| 4,263,467 | 4/1981 | Madgavkar et al. | 585/525 |
| 4,265,871 | 5/1981 | Felice, Jr. et al. | 423/531 |
| 4,308,414 | 12/1981 | Madgavkar et al. | 585/525 |
| 4,365,105 | 12/1982 | Morganson et al. | 585/525 |
| 4,384,162 | 5/1983 | Vogel et al. | 585/830 |
| 4,394,296 | 7/1983 | Madgavkar et al. | 252/433 |
| 4,429,177 | 1/1984 | Morganson et al. | 585/525 |
| 4,433,197 | 2/1984 | Vogel et al. | 585/823 |
| 4,454,366 | 6/1984 | Vogel et al. | 585/525 |
| 4,520,006 | 5/1985 | Laviron et al. | 423/531 |
| 4,781,909 | 11/1988 | Evans et al. | 423/531 |
| 4,956,513 | 9/1990 | Walker et al. | 585/525 |
| 4,973,743 | 11/1990 | Turner et al. | 560/202 |
| 4,981,578 | 1/1991 | Tycer et al. | 208/262.1 |
| 5,068,487 | 11/1991 | Theriot | 585/510 |
| 5,120,897 | 6/1992 | Del Rossi et al. | 585/726 |
| 5,180,403 | 1/1993 | Kogure | 55/53 |
| 5,254,784 | 10/1993 | Nurminen et al. | 585/252 |
| 5,371,052 | 12/1994 | Kawamura et al. | 502/20 |
| 5,705,727 | 1/1998 | Holub et al. | 585/525 |
| 5,811,616 | 9/1998 | Holub et al. | 585/504 |

FOREIGN PATENT DOCUMENTS

| | | | |
|---|---|---|---|
| 364889 | 5/1990 | European Pat. Off. | C07C 2/20 |
| 493024 | 7/1992 | European Pat. Off. | C10G 71/04 |
| 594065 | 4/1994 | European Pat. Off. | B01J 27/32 |

OTHER PUBLICATIONS

Topchiev, A. V., "Boron Trifluoride and its compounds as catalysts in Organic Chemistry", (1959), pp. 64–70 –no month.

*Primary Examiner*—Walter D. Griffin
*Assistant Examiner*—Nadine Preisch
*Attorney, Agent, or Firm*—James R. Henes; Joseph DiSalvo; Stephen L. Hensley

[57] ABSTRACT

This invention concerns a process for recovering $BF_3$ from a $BF_3$/promoter complex catalyzed α-olefin oligomerization product stream, which process comprises thermally cracking the complex in the product stream to yield $BF_3$ gas, and contacting the $BF_3$ gas with a cold α-olefin stream containing a promoter.

12 Claims, 1 Drawing Sheet

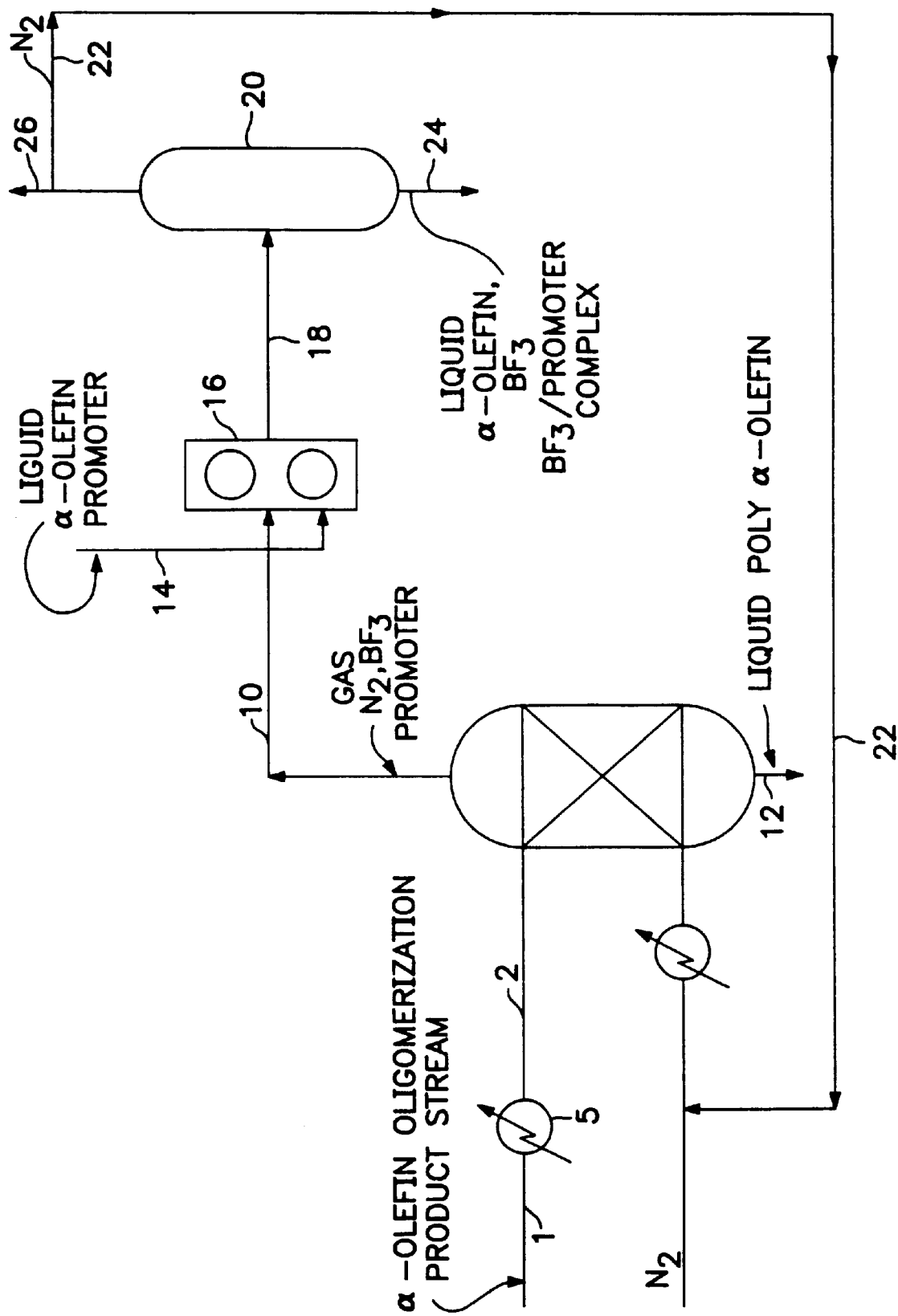

BF$_3$ REMOVAL FROM BF$_3$ CATALYZED OLEFIN OLIGOMER

BACKGROUND OF THE INVENTION

Alpha-olefin oligomers and their use as hydraulic fluids and synthetic lubricants (synlubes) are well known. U.S. Pat. No. 2,927,129 reports the oligomerization of C$_{5-14}$ α-olefins using a dialkyl peroxide catalyst to make a synlube. U.S. Pat. No. 3,113,167 describes an α-olefin oligomer process using a titanium halide and an aluminum compound as the oligomerization catalyst.

The preferred catalysts for making α-olefin oligomers are Friedel-Crafts catalysts such as boron trifluoride (BF$_3$) as disclosed in U.S. Pat. No. 3,149,178. Optimum properties are obtained starting with 1-decene although mixtures of α-olefins have been used, cf. U.S. Pat. No. 3,330,883.

The preferred Friedel-Crafts catalyst is BF$_3$. Pure BF$_3$ is not an effective oligomerization catalyst. A small amount of polar compound is necessary as a promoter which forms a complex with the BF$_3$. U.S. Pat. No. 3,382,291 describes the user of alcohol promoters such as decanol. Other reported promoters are mordenite (hydrogen form), water, phosphoric acid, fatty acids (e.g., valeric acid), ketones, organic esters, ethers, polyhydric alcohols, silica gel and the like.

While the BF$_3$ based catalysts are preferred, they are expensive and, in many cases, not easily reused and must be disposed of, which in itself presents a significant problem. Thus, it would be beneficial to be able to recover BF$_3$ values in a manner which would allow for catalyst recycle.

The product stream from the olefin oligomerization is a liquid and contains a mixture of α-olefin oligomers, dissolved BF$_3$ and the BF$_3$ and promoter complex. The dissolved BF$_3$ is not present in a great amount but can be recovered by any of several different recovery methods. Vogel, et al., U.S. Pat. No. 4,454,366 and U.S. Pat. No. 4,384,162, describe the use of polyvinyl alcohol to remove BF$_3$ from an oligomerization reaction. Vogel, et al., U.S. Pat. No. 4,433,197, contacts the reaction product with silica to remove the BF$_3$. Morganson, et al., U.S. Pat. No. 4,429,177, and Madgavkar, et al., U.S. Pat. No. 4,213,001 and U.S. Pat. No. 4,308,414, use silica as an absorbent for BF$_3$ in an oligomerization process. Madgavkar, et al., U.S. Pat. No. 4,394,296, describe the use of wet silica as a co-catalyst with BF$_3$ in an oligomer process. The silica can be filtered off and recycled as the catalyst. Madgavkar, et al., U.S. Pat. No. 4,263,467, remove BF$_3$ by trickling the reaction product over an inert metallic or ceramic bed whereby the BF$_3$ is said to evaporate and can be recovered. Tycer, et al., U.S. Pat. No. 4,981,578, teaches the recovery of BF$_3$ by contacting the oligomer product stream with solid or aqueous KF, NaF or NH$_4$F. Walker, et al., U.S. Pat. No. 4,956,513, teaches BF$_3$ recovery by extracting BF$_3$ from the oligomer reaction product by washing same with water.

From this it can be seen that a great deal of effort has gone into developing a method for removing BF$_3$ from an olefin oligomerization process in an environmentally safe manner.

The Invention

This invention relates to a process for the recovery of BF$_3$ from a promoted BF$_3$ catalyzed α-olefin oligomerization product stream. The recovered BF$_3$ can come from that which is dissolved in the liquid product stream and that which is present as a BF$_3$/promoter complex. The process features the thermal cracking of at least a portion of the BF$_3$/promoter complex to yield promoter and gaseous BF$_3$. The BF$_3$ gas is effervescent to the extent that it is not dissolved in the stream. With regard to the dissolved BF$_3$, be it from thermal cracking or otherwise, its concentration in the stream will be attenuated as the thermal cracking heats the stream to thereby increase the vapor pressure of the dissolved BF$_3$ so that at least a portion thereof leaves the stream as a gas.

The gaseous BF$_3$ is recoverable for reuse by quenching the gas with a liquid α-olefin stream. Preferably, the olefin stream will be the same as that used to feed the oligomerization reaction. The quenching results in a portion of the gaseous BF$_3$ being dissolved in the stream. The benefits from such a quenching are limited by the solubility of the BF$_3$ in the olefin stream. It is well recognized that such solubility is rather small. As a result, not much of the gaseous BF$_3$ is recovered in this manner.

Instead, it is preferred to quench the gaseous BF$_3$ with a liquid olefin stream which contains a promoter. With this technique, there is obtained a much greater B$_3$ presence in the stream. The promoter forms a complex with the BF$_3$, which complex can be present in the olefin stream in an amount which is much greater than that which can obtained by simply dissolving BF$_3$ in the stream. Thus, much of the gaseous BF$_3$ can be reused and there can be obtained an α-olefin stream which contains dissolved BF$_3$ and the BF$_3$/promoter complex and which, as a result, is suitable for feed to an olefin oligomerization reaction.

DESCRIPTION OF THE DRAWING

The FIGURE is a schematic diagram depicting a process of this invention.

DETAILED DESCRIPTION OF THE INVENTION

Methods of conducting a BF$_3$ catalyzed oligomerization process are well-known. In one mode, BF$_3$ is merely bubbled through the α-olefin reaction mixture containing a promoter during the oligomerization. In a preferred mode, the process is conducted under BF$_3$ pressure. A useful pressure is about 1–100 psig, preferably 5–50 psig and more preferably about 10–20 psig.

Any of the known promoters for BF$_3$ can be used such as water, alcohol (e.g., methanol, ethanol, n-propanol, isopropanol, n-butanol, isobutanol, n-hexanol, 2-ethyl hexanol, n-decanol, n-dodecanol and the like, including mixtures thereof), fatty acids (e.g., valeric, caproic and the like), organic esters (e.g., butyl acetate, methyl valerate, ethyl octanoate, and the like), ketones (e.g., methyl ethyl ketone, methyl isobutyl ketone, and the like), ethers (e.g., dibutyl ether, tetrahydrofuran, dioxane and the like), alkoxylated alcohols (e.g., 2-ethoxyethanol and the like), polyhydric alcohols (e.g., glycol, glycerol, and the like), inorganic acids (e.g., phosphoric and the like), silica, zeolites and the like.

The preferred promoters are water and alcohols containing about 1–8 carbon atoms, such as methanol, ethanol, isopropanol, n-propanol, n-butanol, isobutanol, n-hexanol and n-octanol. The more preferred promoters are alcohols containing about 2–5 carbon atoms. The most preferred promoters are n-proponal and n-butanol.

The amount of promoter should be an amount that causes the BF$_3$ to act as an oligomerization catalyst. This is referred to as a promoter amount. A useful range is about 0.1–2.0 weight percent of the α-olefin.

Alpha-olefins useful in the process are those containing about 6 to 36 and, preferably, 8 to 12 carbon atoms such as 1-octene, 1-decene, 1-dodecene and the like, including mixtures thereof. The most preferred α-olefin is 1-decene or an olefin mixture containing mainly, for example, at least 75 weight percent 1-decene.

The cold liquid olefin stream is preferably at least similar if not identical in constituents and amounts as is specified for the olefin feed stream for the oligomerization reactor.

Even though α-olefins are the main focus of the processes of this invention, it is to be understood that these same processes are likewise applicable to product streams which contain dissolved $BF_3$ and $BF_3$/promoter complex and which are principally a mix of α-olefin and internal olefin or principally internal olefin. Suitable internal olefins are linear or branched and contain 6 to 36 carbon atoms. The internal olefin is a mix of olefin isomers with the double bond being located in various non-α positions.

The preferred reaction temperature is about 20–50° C. and more preferably about 25–40° C. Superior results have been achieved at about 30° C. Lower temperatures will increase the amount of higher oligomers but at the cost of a slower reaction rate. High temperatures give a fast reaction rate but increased yield of dimer.

The amount of $BF_3$ in the reaction mixture should be in excess of the amount required to complex with the promoter. This can be accomplished by saturating the reaction mixture with $BF_3$ such as by continuously bubbling $BF_3$ through the reaction mixture. More preferably, the reaction is conducted in a closed vessel under $BF_3$ pressure. A useful pressure range is about 1–100 psig to about 5–50 psig and most preferably 10–20 psig.

The oligomerization is usually conducted until the monomer content of the reaction mixture drops below about 5 weight percent, more preferably below about 2 weight percent. After the oligomerization reaction has proceeded to the desired extent, the reactor contents, which include the produced oligomer mix, dissolved $BF_3$ and $BF_3$/promoter complex, are removed for treatment in accordance with the instant invention.

The removed contents, which can also be denominated as the α-olefin oligomerization product stream, will have a temperature no higher than about 50° C., and most usually from about 25 to 35° C. To effect the thermal cracking of the contained $BF_3$/promoter complex, the removed product stream is to be heated to the cracking temperature. It is desirable that the cracking temperature not be significantly exceeded as excessive temperatures can adversely affect the product stream. It is preferred that the cracking temperature not exceed 80° C., and most preferably be within the range of from about 50 to about 75° C. The cracking temperature, of course, depends on the thermal stability of the complex used. Thus, it is preferred that the complex chosen be one which gives good catalytic activity but which has an acceptably low cracking temperature. The alcohol promoters, especially n-butanol and n-propanol, are most suitable in this regard.

The α-olefin oligomerization product stream can be heated in any conventional manner, for example, it can be passed through a tube and shell heat exchanger or contacted with a hot, inert heating medium such as $N_2$. It is preferred to use the latter at least at the point where there is a presence of gaseous $BF_3$ as the inert medium can then also act as a stripping medium. When the medium is a gas, however, there will be required a high volume of gas to raise the product stream temperature all the way to the cracking temperature due to the gas low heat capacity as compared to that of the product stream. Therefore, it is preferred that the product stream be heated by efficient means, e.g., a heat exchanger, to a temperature which is near or at the cracking temperature and then contacting the product stream with a hot gaseous heating/stripping medium. For example, a conventional heat exchanger can be used to raise the product stream temperature to, say, 40–65° C. Then, the hot product stream can be contacted with a hot gaseous medium to, as the case may be, either (1) raise the product stream temperature to the needed cracking temperature and effect $BF_3$ stripping or (2) to effect $BF_3$ stripping and to hold the product stream at the cracking temperature. For n-butanol and n-propanol, the cracking temperature will be within the range of from about 50 to about 65° C.

The preferred gaseous heating/stripping medium is $N_2$, $CH_4$, $C_2H_6$, and $CO_2$. Preferred are $N_2$ and $CH_4$, with $N_2$ being most preferred. Again, due to the low heat capacity of the gaseous medium, its temperature can be in excess of the cracking temperature provided that such a temperature does not cause significant thermal degradation of product stream constituents, especially the oligomers and/or promoters. When $N_2$ is the medium, an $N_2$ temperature range of from 50 to 200° C. and, most preferably within the range of from about 75 to about 150° C. can be used. The same can be said for any other suitable medium having a heat capacity similar to that of $N_2$.

To insure high efficiency and economy, it is preferred that the pre-heated product stream be contacted with the hot gaseous medium in a stripping column in a countercurrent manner. The product stream can be fed to the column at a point which is above the feed point for the gaseous medium feed. To enhance the contact between the two phases and to aid the stripping function, the stripping column can be provided with conventional internals, such as packing or trays. The heating/stripping medium, $BF_3$, promoter and some olefin will leave the upper portion of the stripping column as a gas, while a refined, α-olefin oligomerization product will leave the lower portion of the column as a liquid.

Depending on the identity of the promoter and olefin in the original product stream and the stripping gas used, it may be beneficial to operate the stripping column under atmospheric pressure or under a moderate vacuum, say 5 to 10 psia.

The gas from the thermal cracking step is next treated to recover its $BF_3$ constituent. A most beneficial recovery technique is to contact the gas with a cold, liquid olefin stream which contains promoter. Should there be no promoter present, then the $BF_3$ carrying capacity of the olefin stream will be limited to that amount of $BF_3$ which is dissolved into the stream. With an adequate amount of promoter in the olefin stream, the $BF_3$ (as the $BF_3$/promoter complex) carrying capacity of the olefin stream can be sufficient in that the stream can be fed directly to the original oligomerization reaction. The preferred amount of promoter is the same amount as that mentioned in the discussion of the oligomerization reaction.

Note that some promoter can be provided to the liquid olefin stream by the gas stream from the thermal cracking step. The amount of promoter present in the gas from the thermal cracking step depends on the operating temperature and pressure of the stripping column. Thus, the amount of promoter which needs to be in the cold olefin stream prior to its contact with the thermal cracking gas is at least the difference between the amount of promoter needed for the olefin oligomerization feed stream and the amount which is provided by the thermal cracking gas.

The foregoing, which concerns the amount of promoter needed, pre-supposes that there will be an adequate amount of $BF_3$ available to provide for the complex and dissolved $BF_3$ levels needed for a suitable olefin feed stream. If there is an insufficient amount of $BF_3$ in the thermal cracking gas, then the amount of promoter needed in the cold olefin stream can be likewise reduced if desired, or, preferentially, additional $BF_3$ can be added to the complex with the excess promoter prior to the oligomerization reactor.

Generally, a suitable amount of promoter in the cold olefin stream is within the range of from about 0.05 to about 2.0 wt % and, preferably, within the range of from about 0.15 to about 1.0 wt %. The weight percentages being based on the weight of the olefin.

The contact between the cold olefin stream and the thermal cracking gas can be accomplished in a absorber/direct-contact condensation column. This column preferably has internals, such as trays or packing, to enhance contact between the two phases. Preferably, the cold olefin stream is at a temperature within the range of from about 0 to about 50° C. and, most preferably, within the range of from about 15 to about 35° C. The column operates at a pressure within the range of from about 2 to about 20 psia, and preferentially, within the range of about 5 psia to about 15 psia. The gaseous stream leaving the upper portion of this column will contain mainly nitrogen and a small amount of $BF_3$. From the lower portion of the column will exit a liquid olefin stream containing dissolved $BF_3$ and $BF_3$/promoter complex.

There are other apparatuses in which the absorption/condensation step can occur. A particularly preferred apparatus is a liquid ring vacuum pump, which is also known as a liquid piston vacuum pump. The thermal cracking gas is sent to the intake side of the pump, with the cold olefin being fed to act as the liquid ring or piston. Discharged from the pump is a liquid gas mix which can be sent to a knock-out drum for separation. This the of pump is advantageous because it enhances the mixing and contact between the cold olefin and the thermal cracking gas and because it can be used to apply the optional vacuum to the apparatus, e.g., stripping column, to which the olefin oligomerization product stream and heating/stripping medium are fed. The discharge side of the pump is preferably at super-atmospheric pressure.

Referring now to FIG. 1, there can be seen a schematic depiction of a process of this invention. The temperatures, pressures, concentrations, promoter identity, and other process parameters discussed previously all apply to the depicted process and, for the sake of brevity, will not be repeated.

A liquid α-olefin oligomerization product stream is first fed via line 1 to heater 5, which raises the oligomer temperature, and then, is fed via line 2 to thermal cracking/stripping packed column 8. This feed occurs above a hot $N_2$ feed, via line 4, to the same column. In line 4 is $N_2$ heater 6 which raises the N, (including recycled $N_2$) temperature to the level described earlier. The flow in packed column 8 is counter current flow. Withdrawn from packed column 8, via line 12, is poly α-olefin oligomer having a greatly reduced $BF_3$ content. Exiting the upper portion of packed column 8 is a gas comprised of $N_2$, $BF_3$ and some promoter. The gas is conveyed via line 10 to liquid ring vacuum pump 16. Also fed to vacuum pump 16 via line 14 is cool liquid α-olefin and promoter. By way of vacuum pump 16 and line 10 a sub-atmospheric pressure can be maintained in packed column 8, if desired. Vacuum pump 16 discharges, generally at super-atmospheric pressure, a liquid-gas mix which is conveyed via line 18 to liquid/gas separator drum 20. $N_2$ and some $BF_3$ and promoter are vented via line 22 from drum 20 as a gas. A small fraction of this stream may be vented to a scrubber to purge impurities if required, via line 26. Most of the gas is recycled via line 22, back to line 4. From the lower portion of drum 20 is withdrawn, via line 24, a liquid α-olefin stream which contains dissolved $BF_3$ and $BF_3$/promoter complex. This liquid olefin stream can be sent to the oligomerization reactor unit.

What is claimed is:

1. A process for recovering $BF_3$ from a $BF_3$/promoter complex catalyzed α-olefin oligomerization product stream, which process comprises:

(a) thermally cracking at least a portion of the complex in the product stream to yield gaseous $BF_3$ wherein said cracking is conducted at a temperature below 80° C.; and (b) contacting gaseous $BF_3$ from (a) with a liquid α-olefin stream having a temperature within the range of from about 0 to about 40° C., the liquid α-olefin stream containing from about 0.05 to about 1.5 wt % promoter.

2. The process of claim 1 wherein the liquid α-olefin stream in (b) is at least predominately 1-decene.

3. The process of claim 1 wherein the promoter portion of the complex thermally cracked in (a) is an alkanol containing 1–8 carbon atoms.

4. The process of claim 3 wherein the alkanol is n-butanol or n-propanol.

5. The process of claim 3 wherein the promoter in the liquid α-olefin in (b) is the same as the promoter in the thermally cracked complex.

6. The process of claim 4 wherein the promoter in the liquid α-olefin in (b) is the same as the promoter in the thermally cracked complex.

7. The process of claim 1 wherein the thermal cracking in (a) is effected by heating the product stream to the cracking temperature of the $BF_3$/promoter complex.

8. The process of claim 7 wherein the heating is effected by contacting the product stream with an inert gas of a sufficient temperature to accomplish the heating needed.

9. The process of claim 1 wherein the contact between the gaseous $BF_3$ and the liquid α-olefin stream in (b) is effected by feeding the gas and the liquid to a liquid ring vacuum pump.

10. A process for recovering $BF_3$ from a $BF_3$/promoter complex catalyzed olefin oligomerization product stream, which process comprises:

(a) thermally cracking at least a portion of the complex in the product stream to yield gaseous $BF_3$ wherein said cracking is conducted at a temperature below 80° C.; and (b) contacting gaseous $BF_3$ from (a) with a liquid olefin stream having a temperature within the range of from about 0 to about 40° C., the liquid olefin stream containing from about 0.05 to about 1.5 wt % promoter.

11. The process of claim 10 wherein the olefin stream in (b) is selected from the group consisting of α-olefin, internal olefin or a mixture thereof.

12. The process of claim 11 wherein the α-olefin contains 6 to 36 carbon atoms and wherein the internal olefin contains 6 to 36 carbon atoms.

* * * * *